United States Patent [19]

Pantages et al.

[11] Patent Number: 5,098,391
[45] Date of Patent: Mar. 24, 1992

[54] DISPENSING SYSTEM FOR PACING LEAD

[75] Inventors: Anthony J. Pantages, Mountain View; Darrell H. Ogi, Sunnyvale, both of Calif.

[73] Assignee: Abbott Laboratories, Abbott Park, Ill.

[21] Appl. No.: 506,400

[22] Filed: Apr. 9, 1990

[51] Int. Cl.⁵ ............................................. A61M 5/178
[52] U.S. Cl. ..................................... 604/159; 604/158; 604/171; 206/571; 206/564; 206/563
[58] Field of Search ............... 604/158, 159, 171, 172; 206/571, 564, 563, 364, 363, 370

[56] References Cited

U.S. PATENT DOCUMENTS

| | | | |
|---|---|---|---|
| 943,202 | 12/1909 | Struss | 242/164 |
| 3,068,316 | 12/1962 | Witt | 174/135 |
| 3,138,253 | 6/1964 | Harautuneian | 206/364 X |
| 3,372,883 | 3/1968 | Ota | 242/47.5 |
| 3,429,516 | 2/1969 | Sharp et al. | 242/47.5 |
| 3,514,171 | 5/1970 | McGaha | 312/209 |
| 3,851,649 | 12/1974 | Villari | 206/571 X |
| 3,897,631 | 8/1975 | Murata | 32/22 |
| 4,113,750 | 9/1978 | Isobe | 206/388 |
| 4,126,221 | 11/1978 | Cerwin | 206/63.3 |
| 4,160,505 | 7/1979 | Rauschenberger | 206/571 |
| 4,174,816 | 11/1979 | Olson | 242/47.5 |
| 4,522,302 | 6/1985 | Paikoff | 206/571 X |
| 4,688,674 | 8/1987 | Stirtz | 206/388 |
| 4,713,059 | 12/1987 | Bickelhaupt et al. | 604/171 |
| 4,925,448 | 5/1990 | Bazaral | 206/364 X |

*Primary Examiner*—John J. Wilson
*Assistant Examiner*—Jeffrey A. Smith
*Attorney, Agent, or Firm*—Harry G. Thibault; Robert E. Wexler

[57] ABSTRACT

A preformed one-piece plastic dispensing tray includes a storage compartment for retaining an elongated, flexible pacing lead therein. A series of spaced apart dividers extend upward from the storage compartment to engage successive serpentine loops of the pacing lead retained in the storage compartment. The construction of the storage compartment permits the pacing lead to be withdrawn therefrom with negligible resistance, and with no twisting, binding, or interference as the lead is inserted into a patient.

19 Claims, 3 Drawing Sheets

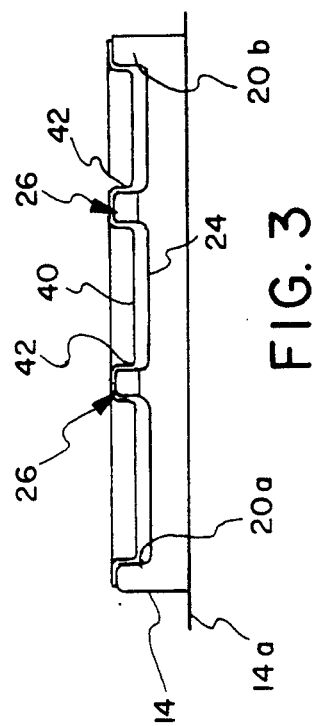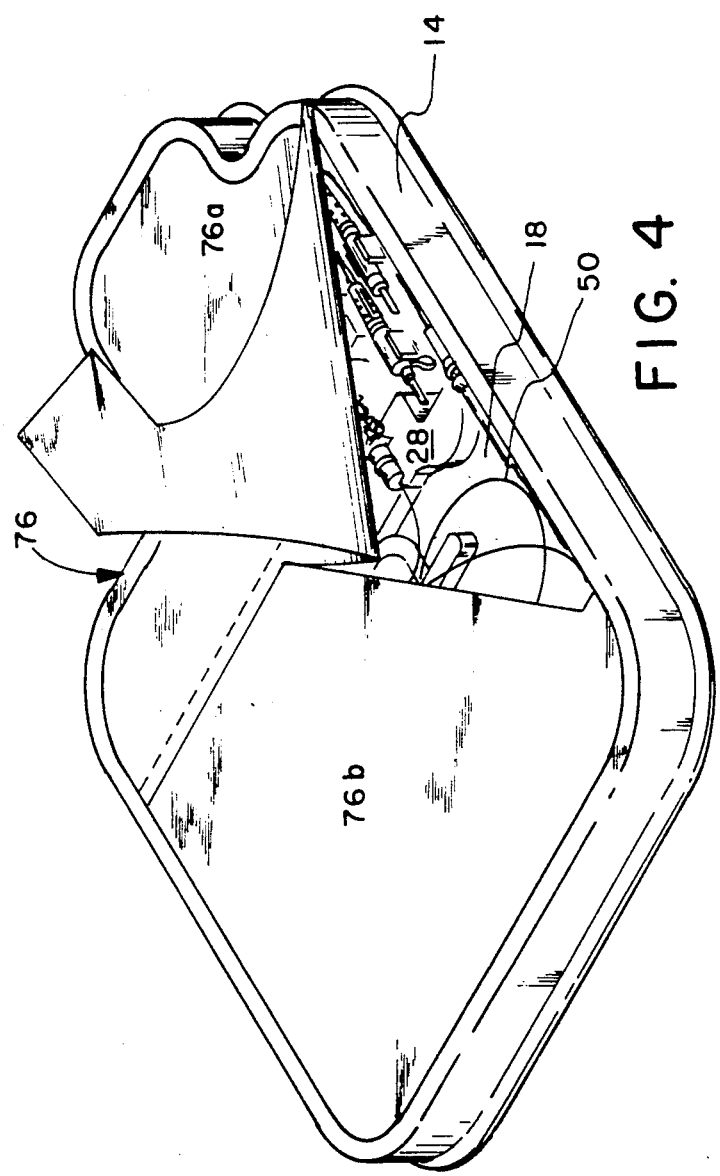

DISPENSING SYSTEM FOR PACING LEAD

BACKGROUND OF THE INVENTION

1. Field of the Invention

The present invention pertains to packages for dispensing an elongated, flexible member such as a probe or catheter, and in particular to an improved dispensing system for a pacing lead.

2. Description of the Prior Art

Because catheters, and the probes associated with them, have an intended use which requires their insertion into a patient, it is critical to optimal performance to deliver the probe from a sterile package to the patient in a manner which limits exposure of the probe to the outside atmosphere. Typically, the catheter has been packaged separately, with the insertion of the associated probe following the insertion of the catheter into the patient. The insertion of the elongated flexible probe into the catheter should be smooth, to minimize installation time, with the inserting probe providing negligible resistance to the user, and with the probe emerging from a package of relative simplicity.

However, efforts to provide a dispensing apparatus for a probe meeting the criteria set forth above have resulted in dispensing systems which include notable constructional complexities. For example, a known system incorporates a reel rotatably mounted on a base in a sterile package. The probe is wound onto the reel for storage with the reel rotating to deliver the probe from the reel when the probe is removed from the package. The reel introduces an undesirable mechanical complexity to the package. Moreover, as the probe is removed from the reel, the probe is capable of binding to prevent withdrawal of the probe from the package. Moreover, failure of this rotating mechanical device could undesirably contribute to the failure of the insertion of the probe into the catheter, thus compromising the sterility of both the catheter and the probe.

Another type of serpentine tubing and surgical cord retractors is disclosed in U.S. Pat. No. 4,174,816 which shows a surgical cord and tube retractor, wherein one end of the cord or tube is secured within a housing, the other end being accessible at a side of the housing, enabling the cord or tube to be withdrawn. The cord or tube passes over a plurality of fixed and longitudinally moving rotating pulleys. As the cord or tube is drawn from the enclosure, the movable pulleys are lifted toward the fixed pulleys, developing a force that tends to pull the cord or tube back into the enclosure. It is desirable to eliminate mechanical complexities from a dispensing system for a pacing lead, and to provide that the pacing lead is not wound around any rotatable object, to be retracted back into the packaging tray upon release by the operator.

Alternative constructions of dispensing packages which eliminated the mechanical reel have been attempted. For example, a dispensing tray having a spiral track for disposing the pacing lead thereon has been attempted. However, in such a configuration, withdrawing the lead from the tray caused the lead to tighten against the wall of the spiral track, to bind up in the tray instead of sliding out of the tray, making insertion of the lead into the catheter difficult.

An alternative configuration proposed locking respective loop ends to locking tabs provided on the walls of a storage compartment for the lead. Such a configuration would result in additional design complexities as well as introducing a requirement of a snap release of the lead from the locking tabs, thus putting additional forces on the pacing lead as it is inserted into the catheter as well as to undesirably affect the smoothness of the delivery of the pacing lead to the catheter.

Another packaging device is shown in U.S. Pat. No. 4,126,221, which describes a package for multiple strands of surgical sutures. Each strand is separately wound in a coil comprising a series of convolutions, each convolution being laterally displaced from adjacent convolutions and placed in sequence within the package. To form the convolutions, each suture is wound in a figure-8 pattern over two dowels, which are then withdrawn. Adjacent sutures are also wound in the figure-8 pattern, and the coils are placed side-by-side in the package with one end of each suture extending to a dispensing orifice from which it can be readily drawn out. As an end of a suture is pulled from the package, the figure-8 pattern collapses or unwinds, permitting the suture to be withdrawn without tangling. However, a packaging concept useful for multiple sutures may not be suitable to prevent entanglement of successive loops of a single elongated pacing lead of considerable flexibility. For example, suture materials can easily be retained in place without the need to provide intervening barriers to maintain the desired configuration and position for the suture. Such a construction is clearly not suitable to position a springy flexible probe of a length substantially longer than the package which is to store the probe.

SUMMARY OF THE INVENTION

The present invention is concerned with an improved dispensing system which avoids the mechanical complexities of the known art, is particularly adapted to the packaging requirements of an elongated flexible member and further eliminates undesirable forces exerted on the pacing lead during insertion into the catheter. Additionally, such a system provides a storage device of relative simplicity, having only two interfacing parts and no moving parts.

In accordance with the present invention, an improved dispensing system includes a preformed plastic tray wherein a storage compartment is provided. Within the storage compartment are a series of dividers or abutments extending upwardly from the base of the compartment. Overlying the storage compartment is a cover with a series of set offs therein corresponding generally to the respective abutments provided on the base of the storage compartment to enable the main body of the cover to extend below the top surface of the abutments. Access is provided at one end of the cover for insertion of an elongated flexible lead into the storage compartment with the length of the lead substantially longer than the longest dimension of the storage compartment.

Opposite ends of the lead are held in place by holding members associated with the dispensing system, with the lead arranged in successive non-interfering loops disposed in the storage compartment, with adjacent ends of the loops engaging respective sidewalls of the storage compartment as well as the sidewalls of the abutments therein to provide a smooth, continuous non-interlinked series of loops from one end to the other of the pacing lead. The dispensing system also includes compartments for holding the end components of the pacing lead, with a top cover overlying the dispensing tray to seal the tray and maintain the pacing lead and the end components therein.

The dispensing system thus described provides an improved package for retaining an elongated flexible member and for permitting insertion of said flexible member into a pulmonary artery pacing catheter with negligible resistance. Such a device avoids the mechanical complexities of the known art and provides a relatively simple storage system which contains no moving parts, and in fact includes only two molded parts. The present invention, along with the advantages associated therewith, is best understood by considering the detailed description set forth below in conjunction with the accompanying drawings briefly described below.

BRIEF DESCRIPTION OF THE DRAWINGS

FIG. 3 is a section taken along the lines 3—3 shown in FIG. 1; and

FIG. 4 is a top left perspective view of the dispensing system of FIG. 1 with a top cover overlying the dispensing tray.

DESCRIPTION OF THE PREFERRED EMBODIMENT

Figure 1:
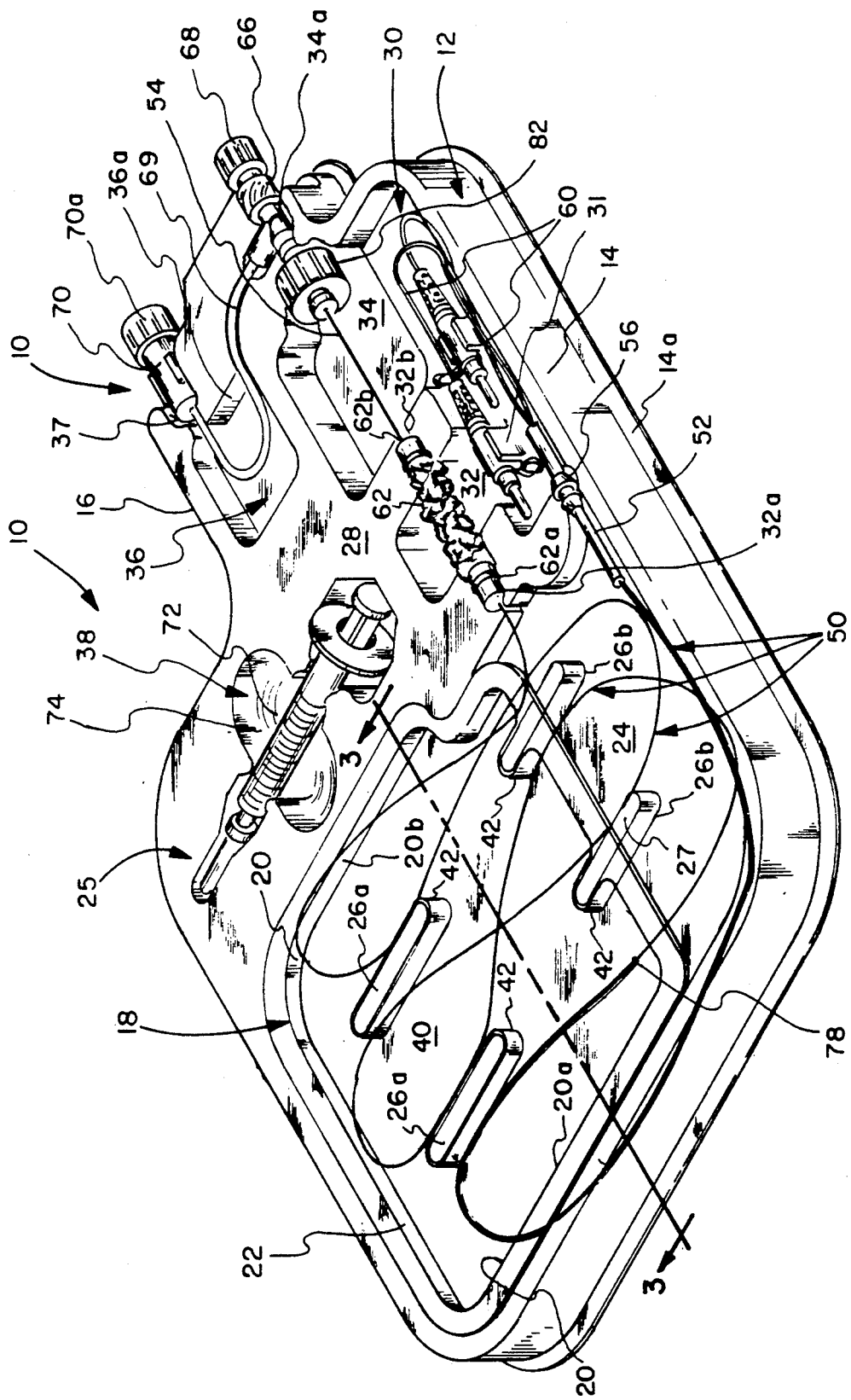
FIG. 1 is a top left perspective view of a dispensing system constructed in accordance with the teachings of the present invention.
Figure 2:
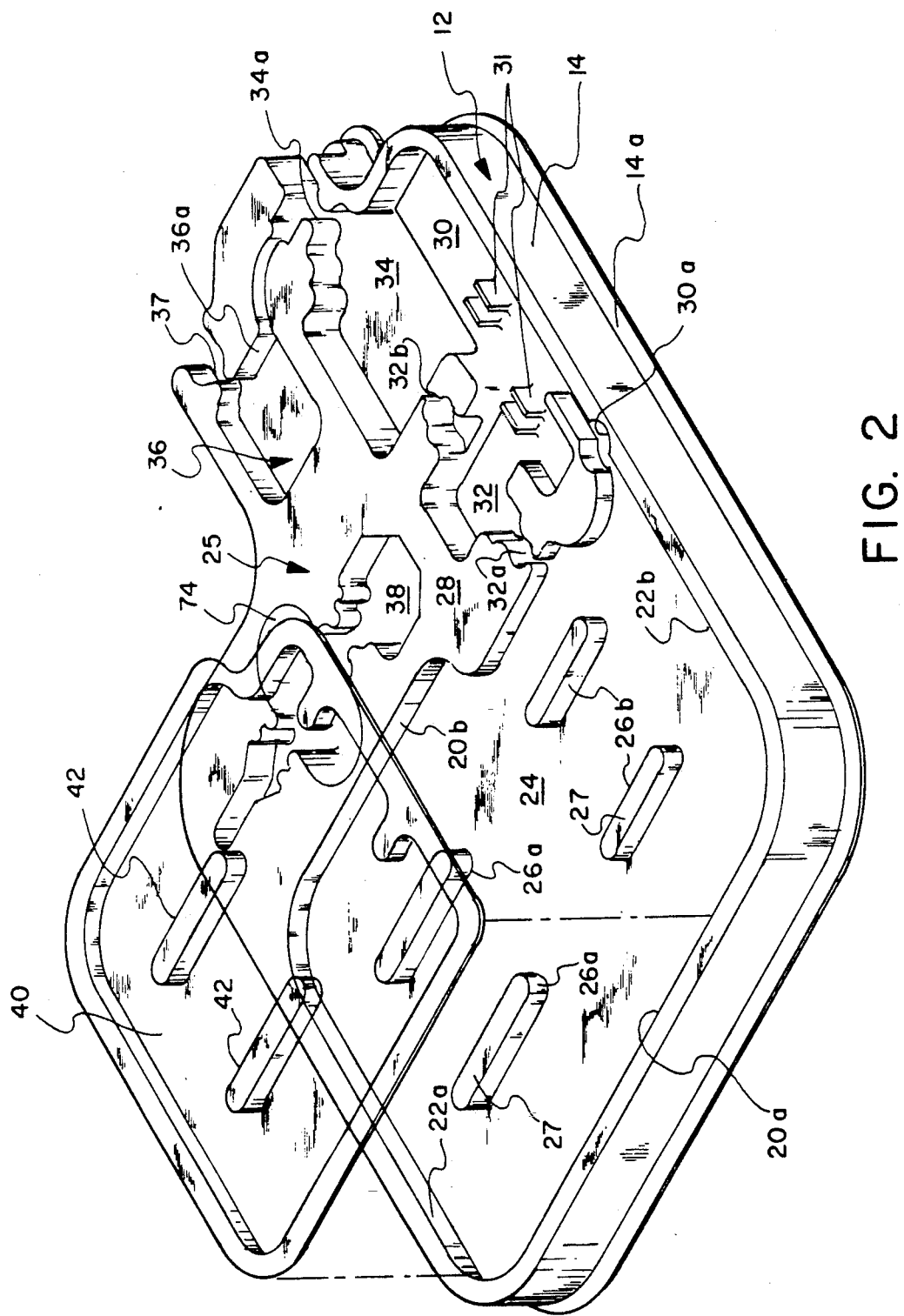
FIG. 2 is an exploded perspective view of the dispensing tray only of the system shown in FIG. 1.

Dispensing system 10 of the present invention is best shown in FIGS. 1 and 2 and comprises a one-piece dispensing tray 12 formed of a transparent plastic. Dispensing tray 12 is a member of generally rectangular shape necked down at one end for reasons described below. A continuous outer sidewall 14 extends around the dispensing tray 12. Disposed opposite necked down portion 16 of the dispensing tray 12 is a substantially rectangular storage compartment 18 which occupies the left-hand half of the dispensing tray. The storage compartment 18 has a base 24. Opposite sidewalls 20 are molded contiguously with opposite end walls 22a, 22b. The walls 20 and 22 extend upwardly from the base 24 and define the length and breadth of the storage compartment 18. The base 24 is disposed about ⅜" below a top wall 25 of the dispensing tray 12 and also displaced about ½" above a bottom flange 14a of the peripheral sidewall 14, to thus place the base 24 slightly above the mid-plane of the dispensing tray. At respective upper and lower ends of the storage compartment 18 are provided a series of molded abutments or dividers 26 extending upwardly from the base 24, to each terminate at a respective upper face 27 which is about 3/16" above the base.

As viewed in FIG. 1, a first pair of upper dividers 26a are so disposed as to be generally equally spaced from sidewalls 20 of the storage compartment 18. The upper dividers 26a are about two inches long, ¼" wide and about 3/16" high, with their respective longitudinal axes generally parallel to the side walls 20 of the storage compartments 18. A pair of lower dividers 26b are similarly disposed on the base 24, and generally in alignment with the abutments 26a, but are about ½" shorter to accommodate the intrusion of a retention portion 28 of the dispensing tray 12 into a lower end of the storage compartment 18.

The retention portion 28 of the dispensing tray 12 comprises a series of storage niches for associated elements of the dispensing system 10. For example, provided on the retention portion 28 of the dispensing tray 12 adjacent the lower end of the storage compartment 18 is an electrical connector storage niche 30. Associated with the electrical connector niche 30 is an end fitting holder 30a disposed between a lower end of the electrical connector niche 30 and adjacent storage compartment 18. Locking tabs 31 are also provided in the electrical connector niche 30. Disposed above the electrical connector niche 30 is a sterile sleeve storage niche 32 having opposite end holders 32a and 32b. The bottom of the sterile sleeve niche 32 opens into the top of the connector niche 30.

Next to the sterile sleeve niche 32 is a generally rectangular manual access niche or area 34 having an end fitting holder 34a at the end of the manual access niche 34 opposite the end holder 32b of the sterile sleeve niche 32. The bottom of the manual access niche 34 also opens into the top of the connector niche 30. Disposed above the manual access niche 34 is a side port storage niche 36. A side port fitting holder 37 is provided adjacent an upper end of side wall 36a of side port niche 36. Disposed adjacent the upper end of the storage compartment 18, and above the sterile sleeve niche 32, is a syringe storage niche 38. The axis of syringe niche 38 is generally transverse to the longitudinal axis of the sterile sleeve niche 32.

Overlying the storage compartment 18 is a cover 40 of clear plastic which generally encloses the upper part of the storage compartment but terminates at the midpoint of lower abutments 26b to provide access to the storage compartment. Set offs 42 in the cover 40 enable the main body of the cover to lie below the respective top walls 27 of the abutments 26 (FIG. 3) to define the storage compartment 18 as a substantially narrow space (about 1/16" high) between the cover and the base 24.

Disposed within the dispensing tray 12 is an elongated flexible member or pulmonary artery (PA), right ventricular (RV) pacing lead 50 having opposite ends 52 and 54. A proximal end 52 is connected to a manifold 56 held in the holder 30a associated with the electrical connector storage niche 30. In turn the manifold 56 connects the pacing lead 50 to electrical connectors 60 secured in the connector niche 30 by locking tabs 31. A notable advantage of the dispensing system 10 of the present invention is the accessibility to the electrical connectors 60. With the electrical connectors 60 already attached to the proximal end 52 of the pacing lead 50, the pacing lead 50 can be connected to a suitable monitor (not shown) to facilitate insertion and placement of the pacing lead 50 into the patient.

The pacing lead 50 extends from the proximal end 52 to coil in serpentine loops about the storage compartment 18 with respective loops first engaging an outer sidewall 20a of the storage compartment, then a first upper abutment 26a next adjacent thereto, to continue in non-interlinked serpentine loops engaging the inner walls of the respective upper abutments 26a and lower abutments 26b, to conclude in a final loop which engages first the inner sidewall 20b and then the upper abutment 26a to then enter a first end fitting 62a of a sterile sleeve 62 disposed in the sterile sleeve storage niche 32. Holder 32a associated with the sterile sleeve niche 32 retains end fitting 62a therein in snap-fit engagement. Pacing lead 50 continues through the sterile sleeve 62, through a second end fitting 62b which is snap fit into holder 32b, and then through the manual access area 34 and into the proximal end of a hemostatis valve 66. A protective cap 68 at the outer end of the valve 66 protects a distal end 54 of the pacing lead 50. Connected to the hemostatis valve 66 through an appropriate fluid input line 69 is a side port 70.

Included in the dispensing system 10 is a syringe 72 disposed in the syringe storage niche 38 to be used to aspirate the pacing lumen of the catheter holding the pacing lead 50 through the side port 70. Note that the storage niche 38 for the syringe 72 includes sufficient side access 74 to enable the user to easily remove the syringe 72 from the dispensing tray 12.

The pacing lead 50 stored in the dispensing tray 12 is to be used in a pulmonary artery (PA), right ventricular (RV) catheter (not shown). The pacing lead 50 in an inherently springy member, and at about 62 inches, substantially longer than the longest dimension of the storage compartment 18, which is about 8-½" long. Therefore it would be difficult to install the pacing lead 50 in the storage compartment 18 of the dispensing tray 12 if means were not provided to somehow contain the pacing lead within the storage compartment during the installation of the pacing lead in the dispensing tray 12. Accordingly the cover 40 is provided to overlay the storage compartment 18, but with sufficient room provided at the lower end of the storage compartment to enable someone loading the pacing lead 50 into the storage compartment to be able to slide the pacing lead under the cover. It is desirable to maintain the height of the storage compartment 18 at a level which will facilitate easy installation of the pacing lead 50 therein. Accordingly the set offs 42 in the cover 40 allow the face thereof to extend below the level of the abutments 26 provided in the storage compartment to provide a spacing between the cover and the base 24 of about 1/16", i.e., which is about 3 times the thickness of the pacing lead 50.

When the pacing lead 50 is stored in the storage compartment 18 of the dispensing tray 12, opposite ends 52 and 54 are fixed, with respective constituent elements such as the electrical connectors 60, the sterile sheath 62, the hemostasis valve 66 and associated side port 70, and the syringe 72 appropriately stored in their respective storage niches. To complete the assembly, a top cover 76 (FIG. 4) is applied to overlie the top wall 26 of dispensing tray 12, following installation of the pacing lead 50 in the storage compartment 18. The top cover 76 is a two-part cover having a first portion 76a and a second portion 76b for reasons set forth below. With the top cover 76 in place, the dispensing system 10 is closed from the outside environment.

The installation of the pacing lead 50 in the pulmonary artery (PA), right ventricular (RV) pacing catheter, with the catheter already in place, is as follows:

Portion 76a of the top sealing cover 76 is removed from the dispensing tray 12 to expose the electrical connectors 60, the sterile sleeve 62, the manual access area 34, the hemostasis valve 66, its associated side port 70, and the syringe 72. Throughout the insertion process, the user has access to the electrical connectors 60, for connection to a suitable processor, thus to facilitate insertion of the pacing lead 50 into the patient.

The pacing lead 50 remains substantially covered under the cover portion 76b. The protective cap 68 on the hemostasis valve 66 is then removed. Next the hemostatis valve 66 is connected to the right ventricular (RV) extension of a pulmonary artery (PA), right ventricular (RV) catheter (not shown). The user draws the pacing lead 50 through the manual access area 34 by hand for insertion into the hemostatis valve 66 and thereafter into the catheter. As the user draws the pacing lead 50 toward the hemostasis valve 66, the body of the pacing lead, disposed in the storage compartment 18, enters the catheter loop by successive loop. Because the abutments 26 prevent interlinking of the loops of the pacing lead 50, the pacing lead can be withdrawn from the storage compartment 18 of the dispensing tray 12 with negligible resistance, and with no binding, twisting, knotting of the pacing lead during the insertion procedure. Provided on the pacing lead 50 is a reference mark 78 about 16" from its proximal end 52. The pacing lead 50 is advanced into the catheter until the reference mark 78 lines up with a complementary zero mark (not shown) provided on the extension of the catheter. A lock nut 82, provided at the rear of hemostasis valve 68, is then tightened down to retain pacing lead 50 in place, and the sterile sheath 62 is then removed from the dispensing tray 12 to connect a sheath distal end fitting 62b to the lock nut 82. The sheath proximal end fitting 62a is then connected to the manifold 56 associated with the electrical connectors 60.

An end cap 70a, associated with the side port 70, is then removed to enable insertion of the syringe 72. Syringe 72 is used to aspirate air from the side port 70, which is then connected to a suitable drip line (not shown) to maintain patency in the pacing lumen of the catheter. With the connection of the drip line to the side port 70, the installation of the pacing lead 50 into the catheter is complete and the dispensing tray 12 can be discarded.

Use of the dispensing system 10 provides an apparatus which enables installation of the pacing lead into a catheter, with negligible resistance against insertion produced by the pacing lead, i.e., the pacing lead does not bind, twist, knot or interfere with the insertion procedure. The dispensing tray 12 is a simple assembly composed of only two molded plastic pieces and has no moving parts, offering users substantial cost savings and eliminating complexities in operation found in devices which require moving parts. Although the preferred embodiment of the present invention defines the flexible member stored in the dispensing system as a pulmonary artery (PA), right ventricular (RV) pacing lead, it is likely that the dispensing system would be useful to store and dispense any elongated flexible member and that the utility of such a dispensing system is not limited to the medical field.

Although one preferred embodiment of the present invention has been described, many changes, modifications, and substitutions may be made without departing from the scope of the present invention. For example, if the stored flexible member were less springy than the member 50 of the present invention, it might be possible to eliminate the cover 40 to provide a one-piece dispensing tray which relied solely on top cover 76 to retain the flexible member therein. The present invention is defined by the appended claims set forth below.

We claim:

1. A dispensing system for retaining an elongated flexible member in a stored position within a dispensing tray, said system comprising:
    a dispensing tray;
    a storing compartment defined within the dispensing tray;
    an elongated flexible member having opposite ends, and of a length substantially longer than the longest dimension of the storage compartment, said elongated flexible member being arranged in multiple loops;

abutment means disposed in the storage compartment to define at least one sub-compartment therein for engaging the flexible member; and a cover overlying the storage compartment and co-operating with the abutment means to retain the flexible member within the storage compartment with the flexible member arranged into multiple loops for storage, and the loops of the flexible member separated from each other by the at least one sub-compartment defined by said abutment means and each said at least no sub-compartment retaining at least one loop of said flexible member to prevent entanglement of said loops and to provide negligible resistance to movement of the flexible member from the storage compartment, thus to facilitate removal of the flexible member from the dispensing tray.

2. A dispensing system as claimed in claim 1 wherein the abutment means comprise a plurality of dividers disposed in the storage compartment, each divider displaced from the other dividers, to provide respective sub-compartments in the storage compartment, each sub-compartment to engage and separate at least one loop of the flexible member, while the flexible member is retained in the dispensing tray.

3. A dispensing system as claimed in claim 1 wherein the storage compartment includes opposite sidewalls formed in the dispensing tray cooperate with the abutment means to provide respective sub-compartments, each sub-compartment to engage and retain at least one loop of the flexible member in the storage compartment.

4. A dispensing system as claimed in claim 1 wherein the cover overlying the storage compartment extends from a first end wall of said tray substantially to a second, opposite end wall of said tray leaving an opening between said cover and said second, opposite end wall to permit access to the storage compartment during loading of the flexible member into the dispensing system.

5. A dispensing system as claimed in claim 1 wherein the cover overlying the storage compartment includes setoffs at the abutment means to dispose the cover below an upper level of the abutment means, to minimize the spacing between the cover and a base of the storage compartment, thereby to restrict unwanted vertical movement of the flexible member within the storage compartment.

6. A dispensing system as claimed in claim 1 wherein the dispensing tray is formed as a transparent plastic enclosure and wherein the storage compartment is substantially rectangular and is disposed on a first portion of the tray, with storage niches disposed on a second portion of the tray.

7. A dispensing system as claimed in claim 6 wherein the second portion of the dispensing tray is necked down to facilitate handling of the dispensing system during insertion of the flexible member into a patient.

8. A dispensing system as claimed in claim 7 wherein means are provided on the dispensing tray for retaining the opposite ends of the elongated flexible member in respective fixed positions during storage.

9. A dispensing system as claimed in claim 8 wherein the retaining means are provided on the dispensing tray proximate each associated storage niche to limit movement of each end stored in a respective retaining means proximate an associated storage niche while the flexible member is stored within the tray.

10. A dispensing system as claimed in claim 9 wherein at least one of the retaining means facilitates movement of the flexible member out of the dispensing tray.

11. A dispensing system as claimed in claim 10 wherein the retaining means comprises a holder adjacent a manual access niche of the dispensing tray for holding a hemostasis valve connectable to one end of the flexible member, the hemostasis valve to facilitate insertion of the flexible member into a patient.

12. A dispensing system as claimed in claim 11 wherein a side port storage niche provided on the dispensing tray holds a side port which provides access to a fluid path around the flexible member for aspiration thereof and to maintain patency.

13. A dispensing system as claimed in claim 12 wherein a syringe storage niche is provided on the dispensing tray for supporting a syringe to be inserted into the side port to aspirate the fluid path around the flexible member.

14. A dispensing system as claimed in claim 13 wherein a sterile sleeve storage niche is provided on the dispensing tray adjacent a manual access area opposite a hemostasis valve to support a sterile sleeve assembly which protects the flexible member during use.

15. A dispensing system as claimed in claim 14 wherein electrical connectors are connected to one end of the flexible member, the electrical connectors disposed in an electrical connector storage niche in the dispensing tray, to be accessible during insertion of the flexible member into a patient, to facilitate said insertion.

16. A dispensing system as claimed in claim 15 wherein end connectors are provided on opposite ends of the sterile sleeve assembly to connect at lest one end of the flexible member to the sterile sleeve assembly when the insertion of the flexible member into the patient is complete.

17. A dispensing system as claimed in claim 1 wherein a two part top cover overlies the top of the dispensing tray in a sealing relationship, with a first portion of the cover overlying the storage compartment and the flexible element therein, and a second portion of the cover overlying a separate manual access area of the tray adjacent to the storage compartment, the two parts of the cover separately removable so as to permit the user access to the separate manual access area of the tray while limiting exposure of the flexible member to the environment outside the dispensing tray.

18. A dispensing system for retaining an elongated flexible member in a stored position within a dispensing tray, said system comprising:

a dispensing tray;

a storage compartment within the dispensing tray;

an elongated flexible member having opposite ends, and of a length substantially longer than the longest dimension of the storage compartment said elongated flexible member being arranged in multiple loops; and abutment means disposed in the storage compartment to define at least one sub-compartment therein for engaging the flexible member, with the flexible member being arranged into multiple loops for storage, and the loops of the flexible member separated from each other by the at least one sub-compartment defined by said abutment means, each said at least one sub-compartment retaining at least one loop of the flexible member to prevent entanglement of said loops and to minimize resistance to movement of the flexible member from the storage compartment, thus to facilitate removal of the flexible member from the dispensing tray.

19. A method for retaining an elongated flexible member in a stored position within a dispensing tray, said method comprising:

defining a dispensing tray;

defining a storage compartment within the dispensing tray;

defining an elongated flexible member having opposite ends, of a length substantially longer than the longest dimension of the storage compartment, for retention within the storage compartment;

disposing abutment means in the storage compartment to define sub-compartments therein for engaging the flexible member;

covering the storage compartment with a cover in engagement with the abutment means to retain the flexible member within the storage compartment; and arranging the flexible member into multiple loops in the storage compartment for storage, at least one loop of the flexible member disposed in a respective sub-compartment to separate said at least one loop from the other loops of the flexible member to prevent entanglement of said loops and to minimize resistance to movement of the flexible member from the storage compartment, thus to facilitate removal of the flexible member from the dispensing tray.

* * * * *